US 6,700,427 B1

(12) United States Patent
Sherman (10) Patent No.: US 6,700,427 B1
(45) Date of Patent: Mar. 2, 2004

(54) WIDEBAND DC-ACCURATE SERIES RESISTANCE COMPENSATOR

(76) Inventor: Adam J. Sherman, 9-379 Labadie St, Montreal, Quebec (CA), H2V 2J9

( * ) Notice: Subject to any disclaimer, the term of this patent is extended or adjusted under 35 U.S.C. 154(b) by 0 days.

(21) Appl. No.: 10/229,092

(22) Filed: Aug. 28, 2002

(51) Int. Cl.[7] ................................................. H03K 5/00
(52) U.S. Cl. ...................................... 327/309; 327/307
(58) Field of Search ................................. 327/551, 362, 327/553, 558, 311, 309, 317, 310; 600/547

(56) References Cited

U.S. PATENT DOCUMENTS

| | | | |
|---|---|---|---|
| 4,510,442 A | * 4/1985 | Neher | 324/99 R |
| 4,896,672 A | * 1/1990 | O-Toole | 600/445 |
| 6,163,719 A | 12/2000 | Sherman | 600/547 |
| 6,424,480 B1 | * 7/2002 | Bhandari et al. | 327/551 |

OTHER PUBLICATIONS

Sigworth, F.J., Electronic Design of the Patch Clamp in Single–Channel Recording, edited by B. Sakmann and E. Neher, 1983, pp 3–35, Plenum Press, New York.

Sherman, A.J., Alvin Shrier and Ellis Cooper, Series Resistance Compensation for Whole–Cell Patch–Clamp Studies Using a Membrane State Estimator, *Biophys. J.*, Nov. 1999, vol. 77:2590–2601, Biophyiscal Society, USA.

Moore, J.W., Michael Hines, and Edward M. Harris, Compensation for Resistance in Series with Excitable Membranes, *Biophys. J.*, Oct. 1984, vol. 46:507–514, Biophysical Society, USA.

Strickholm, A., A Single Electrode Voltage, Current and Patch–Clamp Amplifier with Complete Stable Series Resistance Compensation. Sep. 1995, *J. Neurosci. Methods.*, vol. 61:53–66.

Stefani, R. T., C. J. Savant Jr., B. Shahian, and G. H. Hostetter, Design of Feedback Control Systems, 1994, pp 462–501, Saunders College Publishing, USA.

* cited by examiner

*Primary Examiner*—Dinh T. Le (57) ABSTRACT

A filter means (36) which forms a frequency-selective attenuator (FSA) to attenuate the series resistance compensation signal (Vcomp) of a voltage clamp (5) having an undesired series resistance (Rs). Filter means (36) increases the stability and eliminates the steady-state error of series resistance compensation without compromising the compensated bandwidth, and without requiring excessive bandwidth of the compensation signal (Vcomp) to ensure stability. Filter means (36) also enables the compensated bandwidth and the rate of steady-state error elimination to be selected. Filter means (36) is particularly suited to improving the series resistance compensation of voltage clamps that measure ionic current in biological preparations, allowing rapid ionic current in excitable cells to be voltage clamped.

16 Claims, 7 Drawing Sheets

WIDEBAND DC-ACCURATE SERIES RESISTANCE COMPENSATOR

BACKGROUND

1. Field of the Invention

The present invention relates to voltage clamping circuits that attempt to maintain a desired clamping voltage in the presence of an undesired series resistance. In particular, the present invention relates to voltage clamping circuits that measure ionic current in biological preparations that are compromised by series resistance. The present invention teaches an improved method to compensate for this series resistance which results in wide bandwidth, zero steady-state error, and high stability.

2. Description of the Prior Art

The Voltage Clamp With Series Resistance

Figure 1:
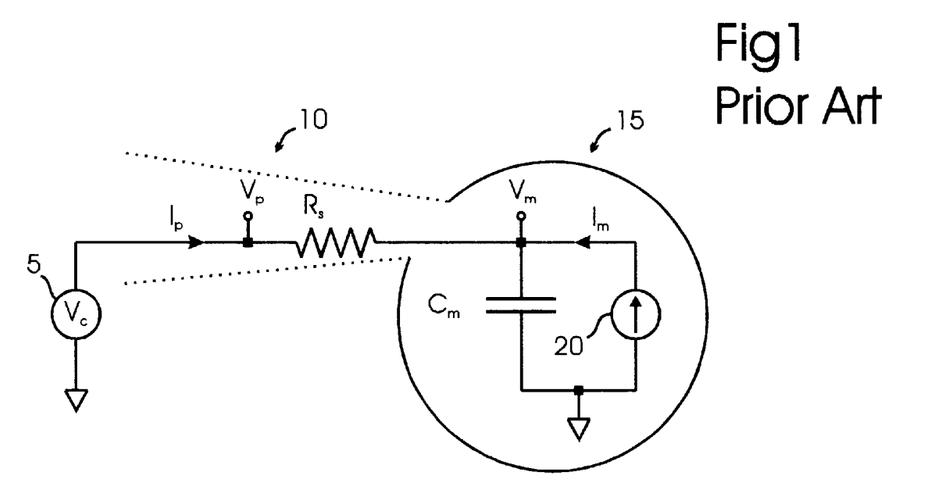
FIG. 1 shows a voltage clamp with a cell and an electrode (prior art).

FIG. 1 shows a voltage clamp often used to measure ionic current in biological preparations. Referring to FIG. 1, a low impedance voltage source 5 generates a command voltage Vc. Voltage source 5 is connected to a biological cell 15 through a single cellular microelectrode, patch electrode or pipette elecrode 10, the fabrication of which is well known in the art. Electrode 10 has an electrode series resistance Rs, an electrode voltage Vp, and an electrode current Ip. Cell 15 has a membrane capacitance Cm, a membrane voltage Vm, and a membrane current Im. Im is related to cell membrane conductance changes—a key quantity to measure in order to understand the electrophysiology of the cell being studied. The generation of membrane current Im by the cell is modeled in FIG. 1 by a current source 20.

If Rs is small enough be ignored, voltage source 5 clamps the membrane voltage Vm at Vc and simultaneously shunts Im which would otherwise flow into Cm. In so doing, Im is measured and characterized as a function of Vm.

In practice the large value of Rs (>10 MΩ) often compromises the effectiveness of the voltage clamp shown in FIG. 1. First, the bandwidth of the voltage clamp and of the current measurement of Im is limited by an access time constant $\tau_a=Rs*Cm$, resulting in an uncompensated bandwidth $fa=1/\tau_a$. The uncompensated bandwidth is often too low to resolve rapidly activating ionic currents. More importantly, the presence of such large Rs values allows Vm to deviate from the desired command voltage Vc due to the finite voltage drop across Rs. Since Im is often a steep nonlinear function of Vm, such voltage deviation will significantly corrupt the measurement of Im.

Series Resistance Compensation

Figure 2A:
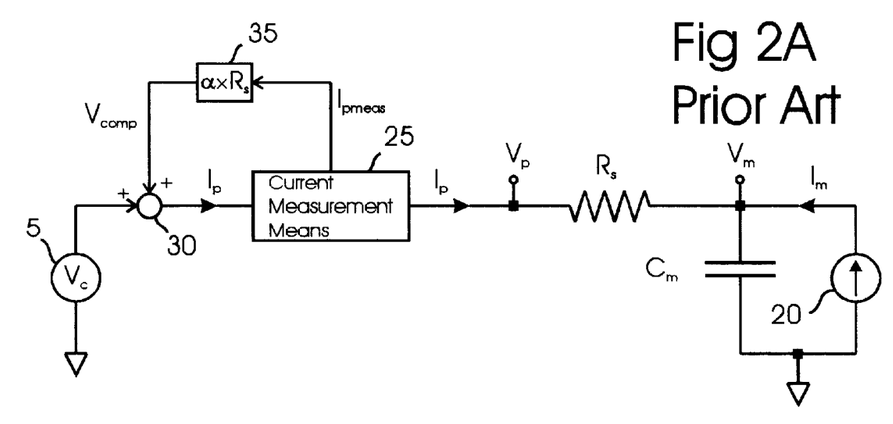
FIG. 2A shows a voltage clamp using standard series resistance compensation (prior art).

FIG. 2A shows a common approach to compensate for the effects of series resistance know as standard series resistance compensation (see *Electronic Design of the Patch Clamp* by F. J. Sigworth, 1983, found in *Single-Channel Recording*, edited by B. Sakrann an E. Neher, p.29–32.) in which a scaled value of the measured pipette current is used as positive feedback to reduce the effective value of Rs. Referring to FIG. 2A, the voltage clamp of FIG. 1 is shown with the addition of a current measurement means 25, a scaler 35, and a summer 30. Current measurement means 25 measures the electrode current Ip to produce a measured electrode current Ipmeas. Scaler 35 multiplies Ipmeas by a scale factor α*Rs, where scale factor a ranges from 0 to 1, to produce a standard series resistance compensation signal Vcomp. Summer 30 adds the command voltage Vc to Vcomp, thus forming a positive feedback loop.

Figure 2B:
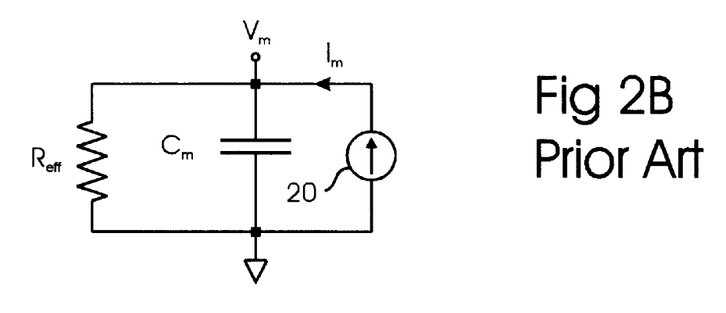
FIG. 2B shows the equivalent circuit of 2A (prior art).

The effect of standard series resistance compensation is illustrated in FIG. 2B which shows the equivalent circuit of FIG. 2A when Vc is set to zero. Referring to FIG. 2B, Cm is shown shunted by a resistor Reff given by $$R_{eff}=(1-\alpha)R_s. \tag{E1}$$

Figure 2C:
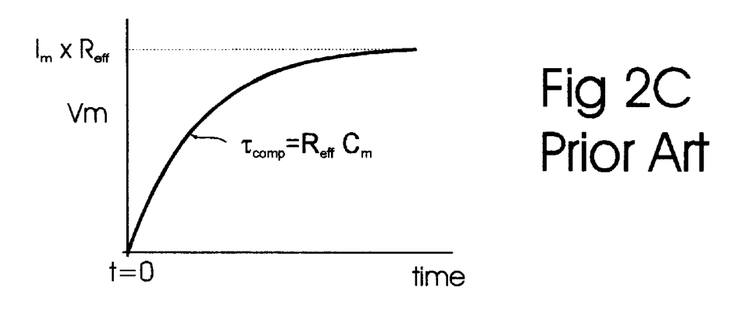
FIG. 2C shows the time-domain step response of FIG. 2B (prior art).

When α=0 Reff=Rs, and as α→1, Reff→0. Therefore the effect of standard series resistance compensation is to reduce the effective value of Rs to Reff, resulting in a compensated time constant $\tau_{comp}=Reff*Cm$ and a compensated bandwidth fcomp=$1/\tau_{comp}$ for the voltage clamp. The step response of standard series resistance compensation is shown in FIG. 2C. Referring to FIG. 2C, the response of Vm to a step change in Im is revealed to be an exponential rise (time constant=$\tau_{comp}$) with an asymptotic error voltage given by Im*Reff (ideally, if Reff were zero the error voltage would be zero as well). Significantly, the error voltage is reduced—not eliminated—by increasing α, accompanied by a simultaneous increase in the compensated bandwidth.

Limitations of Standard Rs Compensation: Stability Constraints at High α Settings While it would be desirable to filly compensate for Rs by setting α=1, (giving 0 error volage and infinite bandwidth) stability constraints limit the maximum a attainable before undamped oscillations occur. Sigworth shows that this oscillation is related to limited bandwidth of the current measurement circuitry and stray capacitance effects of the electrode. For a well-damped response the current measurement bandwidth needs to be~ten times the volage clamping bandwidth. Consequently, high voltage clamp bandwidth (α>~0.8) implies very wide current measurement bandwidth that is difficult to achieve in practice.

Even when attempts are made to create a very wide bandwidth current measurement, they are of limited utility due to another factor which reduces stability at high Rs compensation settings: stray capacitance effects of electrode 10. Electrode 10 has stray capacitance (not modeled in FIGS. 1 and 2) which draws current at high frequencies. This current de-stabilizes standard series resistance compensation. (See frequency response analysis in the Appendix of Sherman et. al. 1999. Series Resistance Compensation for Whole-Cell-Patch-Clamp Studies Using a Membrane State Estimator, *Biophys. J.* 77:2590–2601.) For stable series resistance compensation, it is common practice to compensate for the electrode stray capacitance electronically. The effectiveness of electronic capacitance compensation is compromised at high frequencies, due in part to wide bandwidth requirements, this time in the capacitance compensation circuitry itself. In addition, capacitance compensation performs well when used on a lumped shunt capacitance whereas the electrode stray capacitance is in fact distributed along the length of its immersion depth, in ways that are unpredictable and difficult to characterize mathematically. The distributed nature of the electrode capacitance becomes more pronounced at higher frequencies, which compromises the performance of electronic capacitance compensation. This in turn de-stabilizes standard series resistance compensation at high a settings.

In practice, due both to the difficulties of achieving very wide bandwidth current measurement and of achieving accurate capacitance compensation at high bandwidths, standard series resistance compensation is limited to ~90% (α=0.9).

Limitations of Standard Rs Compensation: Lowpass Filtering the Feedback Signal A common method used to increase the stability of standard Rs compensation is to lowpass filter the signal Vcomp. This approach is used by the Axopatch amplifier series produced by Axon Instruments (Foster City, Calif.), where the "lag" control sets a time constant for a lowpass filter that acts on the Rs compensation signal. While such lowpass filtering avoids high-frequency oscillations, it is of limited utility since the filter then reduces the voltage clamp bandwidth. (See the Theory section of this patent for a discussion of how lowpass filtering relates to and differs from the present invention).

Limitations of Standard Rs Compensation: Excitable Cells—Steady-State Error vs. Bandwidth When working with excitable cells, such as cardiac myocytes responsible for heartbeat generation or nerve cells responsible for nerve signal propagation, a change in Vm of only a few millivolts leads to an extremely large (>100 fold) and rapid (<300 µs) increase in Im that underlies the generation of the action potential. Thus, when voltage clamping excitable cells it is necessary to maintain the change of Vm in response to a change in Im at less than a few millivolts within a time window of ~200 µs, otherwise an unclamped action potential will be generated, leading to loss of volage control, and corruption of the recorded ionic currents.

The steep voltage dependence of Im versus Vm in excitable cells imposes extremely severe steady-state error requirements that are usually impossible to achieve using standard Rs compensation. To illustrate, consider that a typical patch electrode (Rs)=5 Meg) still has an effective series resistance of 0.5 MΩ when used with 90% standard Rs compensation (the maximum level that can normally be obtained before the onset of oscillations). Since excitable cells routinely have Im values >20 nA, the corresponding steady-state error will be >10 mV (20 nA*0.5 MΩ)—more than enough to trigger an unclamped action potential in the cell. To maintain voltage control, it is necessary to lower series resistance errors in response to ionic current flow to less than 2 mV, which corresponds in this case to 98% Rs compensation and a current measurement bandwidth of >300 kHz (10* fcomp~30 kHz). Not only is such high bandwidth unattainable due to the technical difficulties listed above, it is actually not needed to successfully voltage clamp rapid ionic current, a voltage clamp bandwidth of ~10 kHz is sufficient. Therefore, a need exists to provide Rs compensation with very low steady-state error achieved within ~200 µs, but without requiring excessive bandwidth in order to successfully voltage clamp ionic current in excitable cells.

Steady-State Rs Compensation

Moore et. al (Moore, J. W., M Hines, and E. M. Harris. 1984. Compensation for resistance in series with excitable membranes. *Biophys. J.* 46:507–514) and Strickholm (Strickholm, A. 1995. A single electrode voltage, current and patch-clamp amplifier with complete stable series resistance compensation. *J Neurosci. Methods.* 61:53–66) each describe similar modifications to standard Rs compensation wherein an electronic bridge is used to subtract the computed membrane capacity current from the signal Vcomp, assuming a fixed membrane conductance; these modifications are collectively referred to here as steady-state Rs compensation. Steady-state Rs compensation has the advantage achieving 100% Rs compensation in the steady-state, thereby eliminating the steady-state error normally associated with standard Rs compensation. The utility of this approach is limited, however, due to the fact that the bridge circuit significantly compromises the voltage clamp bandwidth (see the Theory section of this patent for details as to why this occurs). As a consequence, it takes several milliseconds for the steady-state error to be removed in response to a change in Im using steady-state Rs compensation. This is far too slow to maintain voltage control in excitable cells.

In summary, there exists a need to provide stable series resistance compensation for a voltage clamp that will enable ionic current in excitable cells to be voltage clamped. While prior art techniques exist to compensate for series resistance, they suffer from numerous disadvantages:

(a) Standard Rs compensation requires excessive bandwidth in order to attain low steady-state error. Such high bandwidth is technically difficult to achieve. Also, at high frequencies the distributed nature of the pipette capacitance dominates, limiting stability.

(b) Standard Rs compensation is very prone to instability due to changes in the electrode parameters at high compensation settings.

(c) Steady-state Rs compensation achieves zero steady-state error at the expense of greatly reducing the voltage clamp bandwidth. At such low bandwidth, it is not possible to voltage clamp rapidly activating ionic current.

Due to these disadvantages, it is extremely difficult to voltage clamp rapid ionic current in excitable cells using prior art series resistance compensation techniques.

OBJECTS AND ADVANTAGES

Accordingly, several objects and advantages of the present invention are:

(a) to compensate for series resistance in a manner that eliminates steady-state error without requiring excessive voltage clamp bandwidth;

(b) to compensate for series resistance in a manner that does not compromise the voltage clamp bandwidth;

(c) to compensate for series resistance in a manner that is not de-stabilized by the distributed capacitance effects of the electrode;

(d) to compensate for series resistance in a manner that is stable with respect to changing electrode characteristics.

A primary aim of the present invention is to enable voltage clamping of ionic current in excitable cells. Further objects and advantages of my invention will become apparent from a consideration of the ensuing description and drawings.

DRAWING FIGURES

In the drawings, closely related figures have the same number but different alphabetic suffixes.

REFERENCE NUMERALS AND PARAMETERS IN DRAWINGS 5 voltage source; generates command voltage Vc
10 electrode; used to access the cell
15 cell
20 current source; generates the membrane current Im
25 current measurement means; measures electrode current Ip
30 summer; adds command voltage Vc to the standard series resistance compensation signal Vcomp
35 scaler; scales measured electrode current Ipmeas (FIGS. 2A, 3A) or electrode current Ip (FIGS. 6A, 6B, 6C) to produce the standard series resistance compensation signal Vcomp
36 filter means; frequency-selective attenuator (FSA) of the present invention
40 subtractor; subtracts membrane voltage Vm (FIGS. 4A, 4B, and 5A) or estimated membrane voltage Vmest (FIG. 6A) from command voltage Vc
41 pro_controller; proportional controller
42 PI_controller; proportional-integral controller
45 transfer function block; s-domain transfer function of membrane voltage Vm to electrode volage Vp
46 transfer function block; s-domain transfer function of electrode current Ip to electrode voltage Vp
50 subtractor; subtracts standard series resistance compensation signal Vcomp from electrode voltage Vp to form estimated membrane voltage Vmest
55 transfer function block; s-domain transfer function of an inner feedback loop
Vc command voltage
Ip electrode current
Vp electrode voltage
Rs electrode series resistance
Cm membrane capacitance
Vm membrane voltage
Im membrane current
Ipmeas measured electrode current
α scale factor; ranges from [0,1]
Vcomp standard series resistance compensation signal
Vcomp' signal Vcomp after attenuation by filter means 36
Reff effective series resistance.
$\tau_{comp}$ compensated time constant
$T_{fsa}$ transfer function of frequency-selective attenuator (FSA)
Vin input node to preferred embodiment of filter means 36
Vout output node of preferred embodiment of filter means 36
R1 first resistor of preferred embodiment; has connection nodes R1a and R1b
R2 second resistor of preferred embodiment; has connection nodes R2a and R2b
C capacitor of preferred embodiment; has connection nodes Ca and Cb
Vcor correction voltage; serves as input to pro controller 41 (FIGS. 4A, 4B) or to PI_controller 42 (FIGS. 5A, 6A)
Vmest estimated membrane voltage

SUMMARY OF INVENTION

In accordance with the present invention, a filter means is provided which attenuates the feedback signal of standard series resistance compensation in a frequency-selective manner, thus forming a frequency-selective attenuator (FSA). The FSA enhances the stability and eliminates the steady-state error associated with standard series resistance compensation without compromising the voltage clamp bandwidth

DESCRIPTION OF THE PREFERRED EMBODIMENT

Figure 3A:
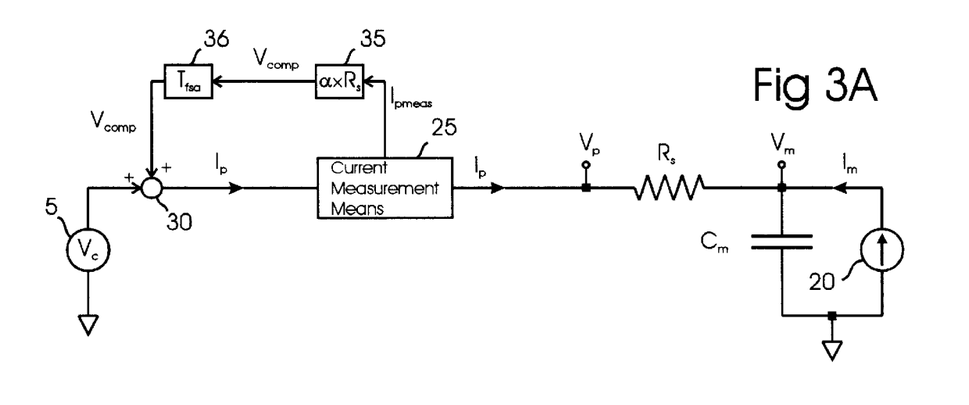
FIG. 3A shows the filter means of the present invention contained within a standard series resistance compensation feedback loop.

FIG. 3A shows the voltage clamp of FIG. 2A redrawn with the addition of a filter means 36 to filter the series resistance compensation signal in accordance with the present invention. Referring to FIG. 3A, filter means 36 takes as input signal Vcomp and outputs a signal Vcomp'. Signal Vcomp' is then used to provide positive feedback in exactly the same manner as described earlier for standard series resistance compensation. Filter means 36 is a unity-gain lowpass filter having a corner frequency below fa. Above the corner frequency, filter means 36 provides increasing attenuation up to fa, and above fa filter means 36 provides a constant attenuation. Thus filter means 36 forms a frequency selective attenuator (FSA). One way to model the frequency-response of the FSA is given by the following s-domain input-output transfer function:

$$T_{FSA} = \frac{\tau_{zero}s + 1}{(\tau_{vc} + \tau_{zero})s + 1} \tag{E2}$$

where $\tau_{zero}$ and $\tau_{vc}$ are time constants and s is the Laplace transform frequency variable. Equation E2 has a real left-hand-plane pole with time constant equal to the sum of $\tau_{vc}$ and $\tau_{zero}$ and a real left-hand-plane zero with time constant equal to $\tau_{zero}$. Details on how to select the values of $\tau_{zero}$ and $\tau_{vc}$ are described in the Theory and the Operation sections of this patent.

Figure 3B:
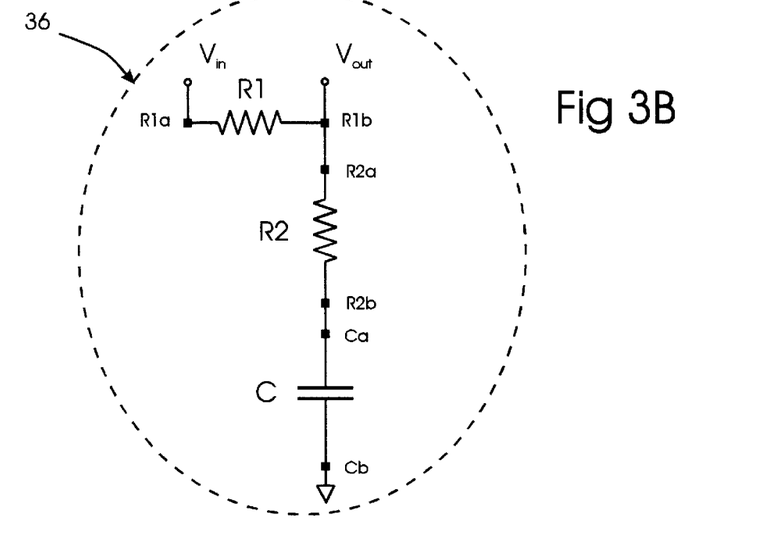
FIG. 3B shows a preferred embodiment of the present invention.

A preferred embodiment of filter means 36 is shown in FIG. 3B. Referring to FIG. 3B, a first resistor R1, a second resistor R2, and a capacitor C are connected in series to form a frequency-selective voltage divider. R1 has a connection node R1a and a connection node R1b. Similarly, R2 has a node R2a and a node R2b, and C has a node Ca and a node Cb. Node R1a serves as an input node Vin to the frequency-selective volage divider. Node R2a is connected to node R1b, which also serves an output node Vout for the frequency-selective volage divider. Node R2b is connected to node Ca, and node Cb is connected to ground.

The s-domain input-output transfer function of the embodiment of FIG. 3B is given by:

$$\frac{V_{out}}{V_{in}} = \frac{R_2Cs + 1}{(R_1 + R_2)Cs + 1} \quad \text{(E3)}$$

Therefore, comparing equation E3 with equation E2 shows that $\tau_{zero}$ is given R2*C and $\tau_{vc}$ is given by R1*C when using the preferred embodiment of the present invention.

THEORY OF OPERATION

The theory underlying the present invention is most clearly illustrated by formulating the voltage clamp problem of a biological cell in terms of a negative feedback control loop. Using this approach, the membrane voltage Vm is assumed to be known, either by direct measurement or by computation; negative feedback then forces Vm to follow Vc. Once cast as a negative feedback control loop, frequency-domain analysis techniques are applied to the open-loop Bode plot to design a Proportional-Integral (PI) controller which ensures zero steady-state error for a given bandwidth (see chapter 7 in *Design of Feedback Control Systems* by Raymond T. Stefani et. al., Saunders College Publishing, 1994 for a description of the PI controller). Given the PI controller coupled with a membrane state estimator (taught by Sherman in U.S. Pat. No. 6,163,719 (1999)), the present invention follows directly after algebraic simplification. The above theoretical formulation also succinctly summarizes and illustrates the limitations of the prior art.

Control of Vm Using Negative Feedback (Proportional Control)

Figure 4A:
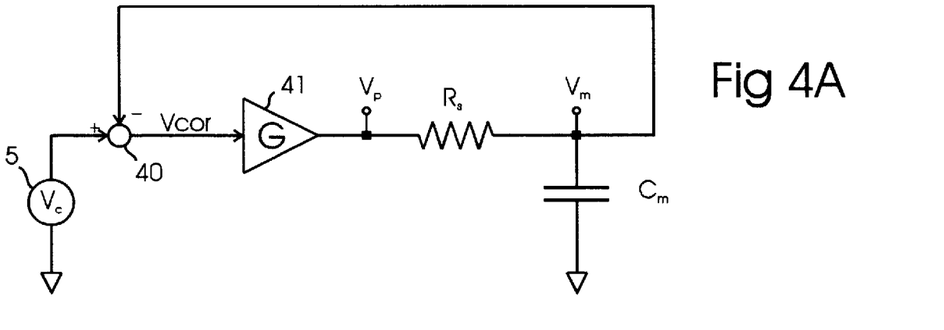
FIG. 4A shows a proportional control twin electrode voltage clamp configuration.

FIG. 4A shows resistance Rs and capacitance Cm of FIG. 1 contained within a negative feedback loop to control Vm (for clarity, current source 20 is omitted). Referring to FIG. 4A, command voltage Vc is compared to the membrane voltage Vm by a subtractor 40, forming a correction voltage Vcor. A pro_controller 41 multiplies Vcor by a scale factor G, forming a proportional controller (see Stefani et. al. for a description of the proportional controller) which forces Vm to follow Vc.

Figure 4B:
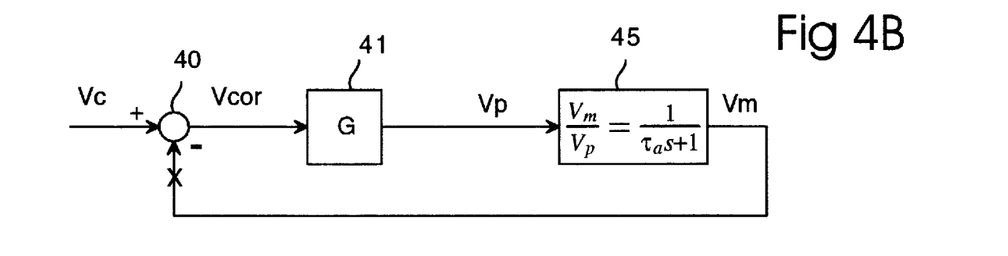
FIG. 4B shows the s-domain block diagram of FIG. 4A.

FIG. 4B shows a Laplace transform block diagram description of FIG. 4A. Referring to FIG. 4B, the same functional elements of FIG. 4A are shown with the addition of a transfer function block 45 which models the behavior of Rs in series with Cm. Block 45 multiplies electrode voltage Vp by the s-domain transfer function of Vm to Vp to output the voltage Vm. Note that it is assumed that Vm is know, as is the case using a twin electrode voltage clamp configuration where Vm is measured directly using a second voltage measuring electrode.

To optimize the closed-loop performance of a feedback control system, it is often easier to work with the open-loop frequency response as displayed in a Bode plot, since the mathematics are more straightforward. Given the open-loop Bode plot, the 0 dB crossover frequency (fco) and the DC gain determine the bandwidth and the steady-state error of the closed-loop system, respectively. The stability of the closed-loop system is determined by applying the Nyquist stability criteria Referring to FIG. 4B, the open-loop transfer function of Vm to Ve is determined by breaking the feedback path at point X, giving:

$$\frac{V_m}{V_c} = \frac{G}{\tau_a s + 1} \quad \text{(E4)}$$

Figure 4C:
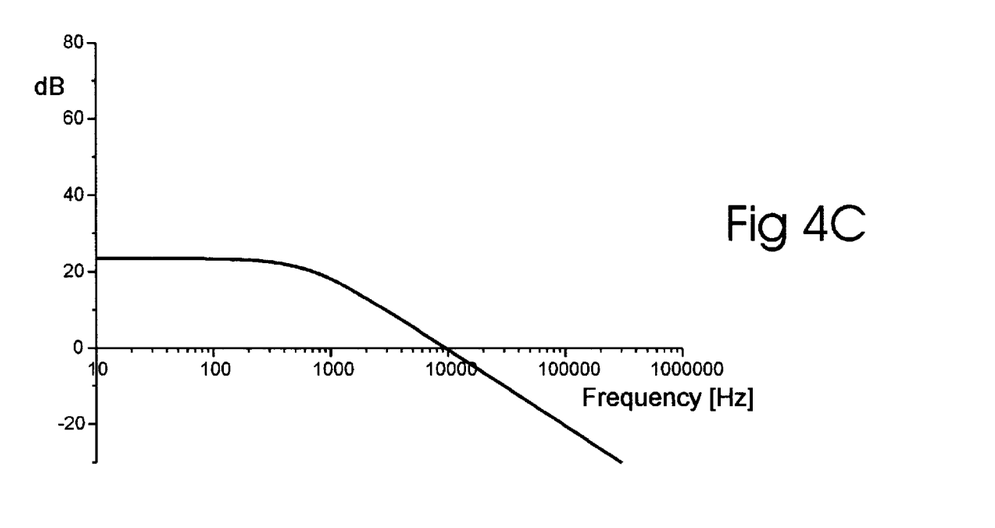
FIG. 4C shows the open-loop Bode plot of FIG. 4B.

The Bode plot of equation E4 is shown in FIG. 4C when Rs=5 MΩ, Cm=50 pF, and G=15, (typical values encountered when patch clamping excitable cells). Referring to FIG. 4C, the fco and DC gain are shown to be 10 kHz and 23 dB, respectively. While an fco of 10 kHz ensures adequate bandwidth to resolve rapid ionic currents, a DC gain of 23 dB is too low to ensure good steady-state performance. Increasing G will improve steady-state performance, but doing so will simultaneously increase fco as well. In practice, increasing fco much beyond 10 kHz is not feasible since higher order phase shifts introduced by the electrode (not modeled in FIG. 4A or 4B) will then reduce phase margin, unacceptably lowering closed-loop stability. Thus using proportional control, it is not possible to ensure adequate steady-state error without over-increasing the bandwidth Control of Vm using negative feedback (PI Control)

To eliminate steady-state error without unduly increasing fco, a PI controller can be used in place of the proportional controller described above. The PI controller transfer function is given by:

$$PI = \frac{\tau_{zero}s + 1}{\tau_{vc}s} \quad \text{(E5)}$$

Figure 5A:
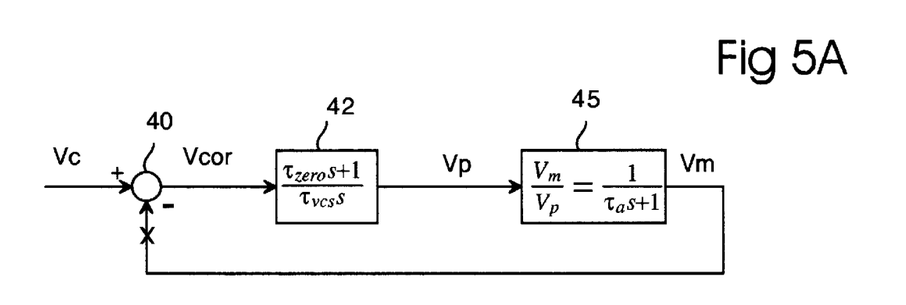
FIG. 5A shows the voltage clamp of FIG. 4B using a PI controller.

FIG. 5A shows a Laplace transform block diagram description of the voltage clamp of FIG. 4B using with a PI_controller 42 in place of pro_controller 41. The open-loop transfer function of FIG. 5A is given by:

$$\frac{V_m}{V_c} = \frac{\tau_{zero}s + 1}{\tau_{vc}s} \frac{1}{\tau_a s + 1} \quad \text{(E6)}$$

Figure 5B:
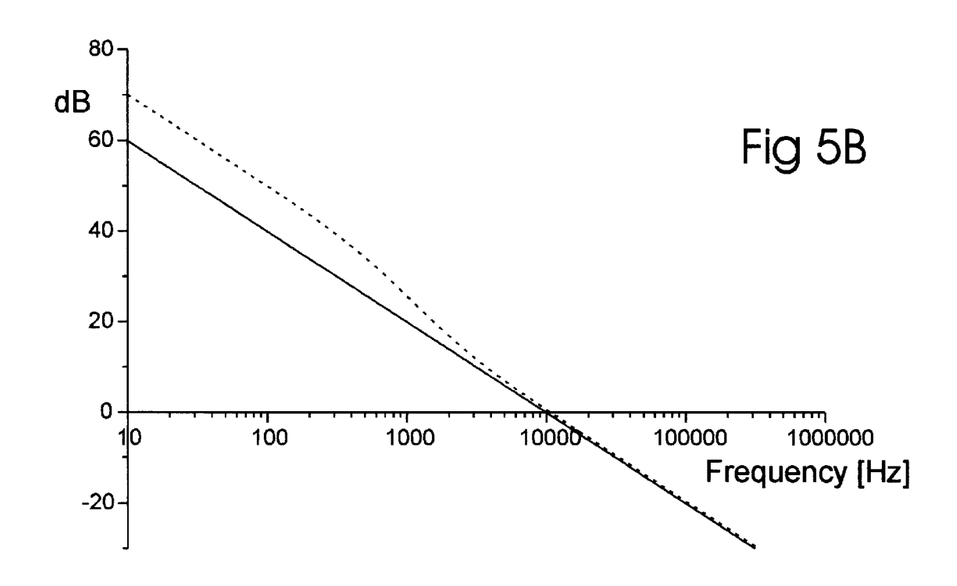
FIG. 5B shows the open-loop Bode plot of FIG. 5A using two sets of constants for the PI controller.

Referring to equation E6, the value of $\tau_{zero}$ is chosen to be approximately equal to $\tau_a$ so that the zero in the numerator cancels the access time constant pole in the denominator. This ensures that the Bode plot has a first order roll-off, guaranteeing a stable, well-damped closed-loop response. The value of $\tau_{vc}$ is chosen to set fco at ~10 kHz, ensuring adequate closed-loop bandwidth. The Bode plot of equation E6 when $\tau_a = \tau_{zero}$ and $\tau_{vc} = 16$ us (fco=10 kHz) is shown by the solid line of FIG. 5B. In contrast to the proportional controller, the PI controller gives infinite DC gain, as shown in FIG. 5B, which ensures that the steady-state error is eliminated without compromising the closed-loop bandwidth.

In general, for a feedback control system the magnitude of the closed-loop error voltage at a specific frequency is inversely proportional to the magnitude of the open-loop gain. Thus high DC loop gain translates to low DC error voltage. Analogously, increasing the open-loop gain at frequencies above DC lowers the error voltage at frequencies above DC. For feedback systems which eliminate DC error as a design criteria, increasing loop gain at frequencies above DC has the effect of removing the DC error voltage faster, which is desirable for the present aim of voltage clamping rapid ionic currents. Using the PI controller, the parameters $\tau_{zero}$ and $\tau_{vc}$ can be selected so as to increase the loop gain below fco in comparison with a first-order response. An example of this is shown in the dotted trace of FIG. 5B, which shows the Bode plot of equation E6 when $\tau_{zero}$ is ~1/3$\tau_a$; $\tau_{vc}$ is again selected to ensure an fco of ~10 kHz. Comparing the dotted trace with the solid trace shows an increase in loop gain of ~10 dB over much of the Bode plot below fco. This translates to a fatter removal of steady-state error in the time domain (see FIG. 7, described in detail later on in this patent, for a depiction of the time-domain performance of the present invention).

PI Control Using a Single Electrode

Figure 6A:
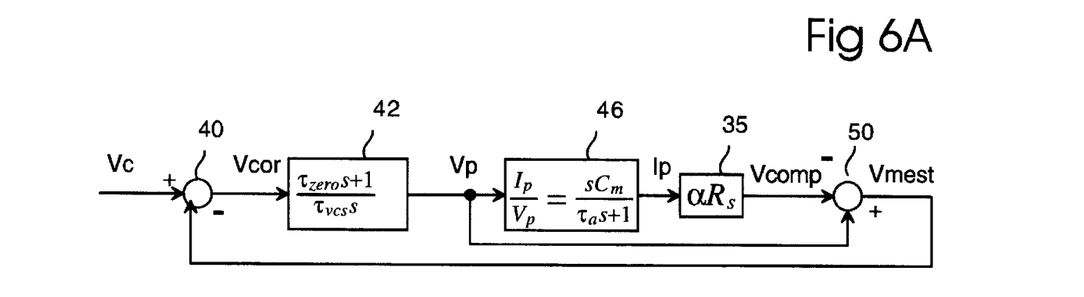
FIG. 6A shows the voltage clamp of FIG. 5A using a membrane state estimator in place of a direct measurement of Vm.

The negative feedback topology of FIG. 4A assumes that Vm is known, as is the case using a twin electrode voltage clamp. However, a twin electrode voltage clamp is often not practical to use owing to the technical difficulties of impaling two electrodes in a single cell. In U.S. Pat. No. 6,163,719 (1999), Sherman teaches a method to compute Vm while using a single electrode voltage clamp equipped with a membrane state estimator. Applying this method to the voltage clamp configuration used in FIGS. 4A,4B, and 5A, eliminates the direct measurement of Vm. FIG. 6A shows the voltage clamp of FIG. 5A redrawn with the addition of scaler 35 (performing the same function as in FIGS. 2A and 3A) and a subtractor 50. The added components form a membrane state estimator to compute Vm instead of measuring it directly. Referring to FIG. 6A, a block 46 multiplies voltage Vp by the s-domain transfer function of Ip to Vp to output the electrode current Ip. Scaler 35 operates the same way as described earlier to output the signal Vcomp. Subtractor 50 subtracts Vcomp from Vp to output an estimated membrane voltage Vmest. (Note that to compute the transfer function of block 46, it is assumed that the stray capacitance of electrode 10 has been compensated for electronically, as described previously for standard Rs compensation). Vmest is then used as negative feedback in the same manner that Vm is used in FIGS. 4A,4B, and 5A. In so doing, the same advantages and improvements a PI controller affords to a twin electrode configuration are conferred to a single electrode voltage claw with series resistance.

Derivation of the Present Invention

Figure 6B:
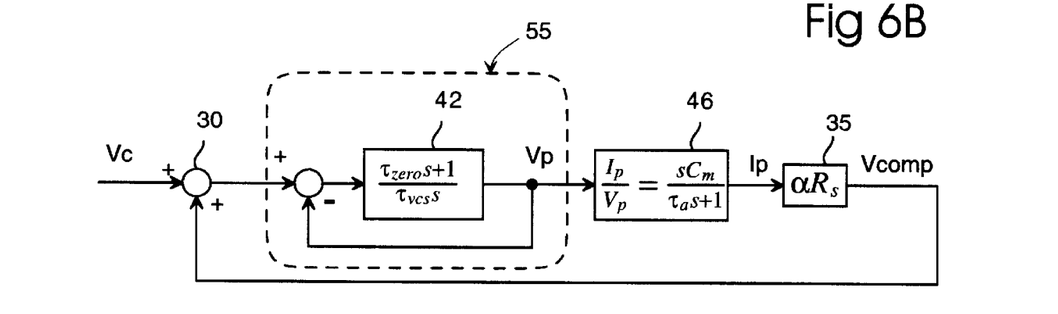
FIG. 6B shows the voltage clamp of FIG. 6A after algebraic manipulation to show an inner feedback loop explicitly.
Figure 6C:
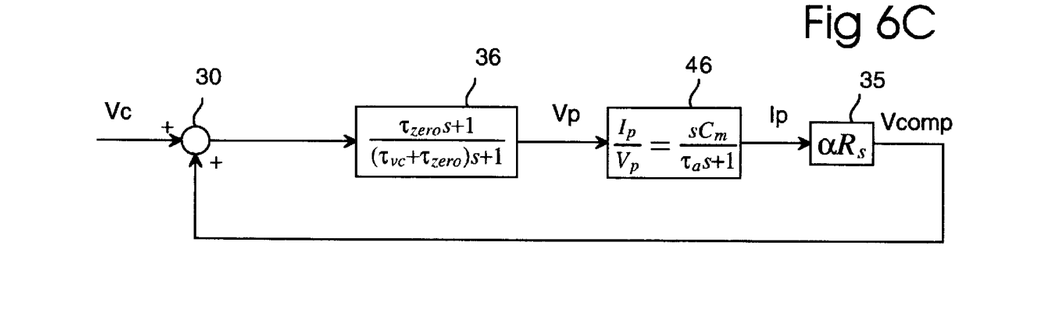
FIG. 6C shows how the filter means of the present invention is derived by reducing the inner feedback loop of FIG. 6B to a single input-output transfer function.

Filter means 36 of the present invention follows directly from FIG. 6A by noting first that the feedback path of Vp into subtractor 50 and then subtractor 40 forms an inner feedback loop. This inner feedback loop is shown explicitly by a transfer function block 55 in FIG. 6B. Note that FIG. 6B is mathematically equivalent to FIG. 6A after algebraic manipulation. Finally, block 55 can be simplified to a single input-output block equivalent to filter means 36 with the transfer function given by equation E2, which is in accordance with the present invention. This is shown explicitly in FIG. 6C, which shows FIG. 6B redrawn but with block 55 simplified and replaced with the equivalent filter means 36 of the present invention. Note that FIG. 6C is equivalent to a Laplace transform block diagram description of the present invention shown in FIG. 3A, but with current source 20 set to 0.

Illustration of the Limitations of the Prior Art: Standard Rs Compensation

The preceding analysis shows that a twin electrode voltage clamp (TEVC) using PI control is mathematically equivalent to a single electrode voltage clamp (SEVC) using 100% standard Rs compensation ($\alpha=1$) equipped with filer means 36 to attenuate the compensation signal Vcomp.

Following a similar analysis it is straightforward to show that a TEVC using proportional control is mathematically equivalent to a SEVC using prior art standard Rs compensation in which at (of the SEVC) is related to G (of the TEVC) by:

$$\alpha = \frac{G}{G+1} \quad \text{(E7)}$$

Therefore, a SEVC using prior art standard Rs compensation has the same performance limitation described for a TEVC using proportional control: in both cases, it is not possible reduce steady-state error without over-increasing the voltage clamp bandwidth.

Illustration of the limitations of the Prior Art: Lowpass Filtering Standard Rs Compensation The prior-art technique of lowpass filtering the Rs compensation signal is equivalent to using filter means 36 of the present invention with $\tau_{zero}=0$. This can be seen by noting that when $\tau_{zero}=0$ $T_{fsa}$ has the transfer function of a lowpass filter. Referring to equation E6 and the corresponding Bode plots shown in FIG. 5B shows that when $\tau_{zero}=0$ the pole-zero cancellation described previously does not occur, thus giving the Bode plot a two pole roll-off above the frequency fa. As a consequence, the Bode plot will intersect the 0 dB axis with a slope of ~40 dB/decade if fco is >fa, resulting in low phase margin and unstable performance. This reveals why lowpass filtering the Rs compensation signal is a poor method to use to increase stability, since it only functions if the voltage clamp bandwidth is kept undesirably low.

Illustration of the Limitations of the Prior Art: Steady-state Rs Compensation

The bridge circuit used to implement prior art steady-state Rs compensation can be shown to reduce mathematically to the filter means of present invention, constrained to having the parameters $\tau_{zero}$ and $\tau_{vc}$ fixed at $\tau_{vc}$. Since $\tau_{vc}$ roughly determines the closed-loop bandwidth (as shown previously), steady-state Rs compensation does not increase bandwidth since the bandwidth without Rs compensation is also set by $\tau_a$. In contrast, the FSA of the present invention allows independent control of the voltage clamp bandwidth, as set by $\tau_{vc}$, while simultaneously eliminating steady-state error.

Time-domain Performance of the Present Invention

To illustrate the improvements in the time-domain performance afforded by the present invention, the error voltage associated with series resistance compensation is calculated using:

(i) $T_{fsa}=1$, $\alpha=0$ (no Rs compensation)

(ii) $T_{FSA} = \frac{\tau_a s + 1}{(\tau_a + \tau_a)s + 1}$, $\alpha = 1$ (equivalent to steady-state Rs compensation of the prior art)

(iii) $T_{FSA}=1$, $\alpha=0.94$ (equivalent to 94% standard Rs compensation of the prior art)

(iv) $T_{FSA} = \frac{\tau_a s + 1}{(16 \text{ } \mu s + \tau_a)s + 1}$, $\alpha = 1$ (the present invention giving 0 error voltage)

(v) $T_{FSA} = \frac{0.33\tau_a s + 1}{(5 \text{ } \mu s + 0.33\tau_a)s + 1}$, $\alpha = 1$ (the present invention giving 0 error voltage in <100 us)

Figure 7:
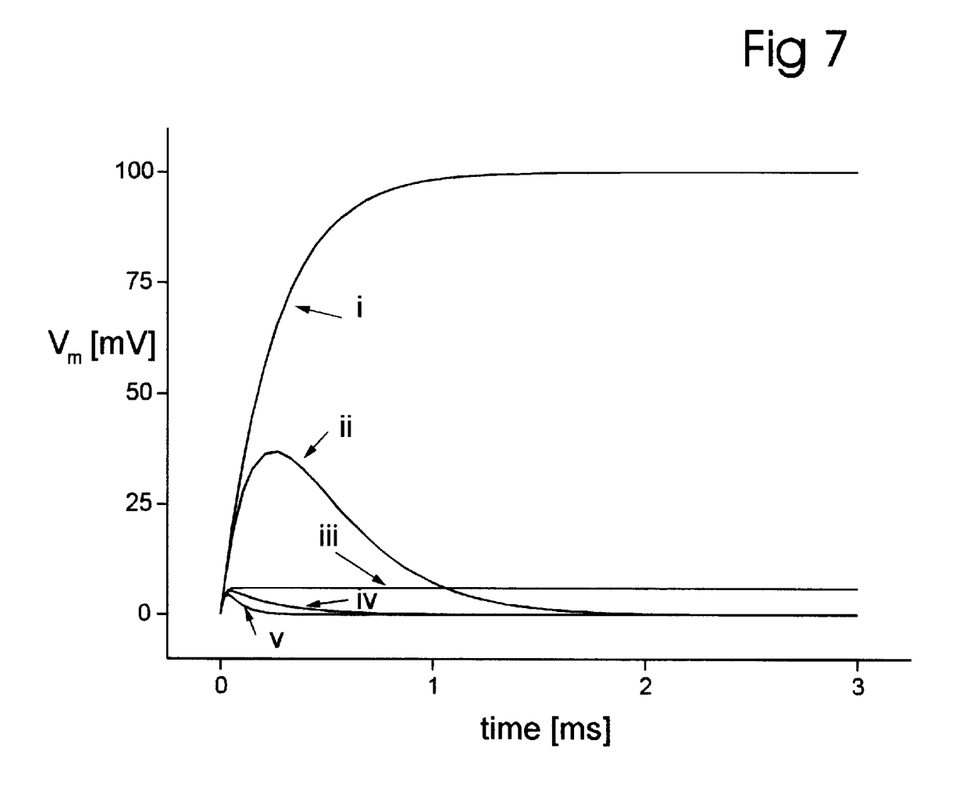
FIG. 7 plots the membrane voltage Vm versus time in response to a step change in membrane current Im for differing filter parameters of the present invention.

The results of these calculations are plotted in FIG. 7, and correspond to the circuit of FIG. 3A under the following condition: Rs=5 MΩ, Cm=50 pF, Vc=0, Im undergoes a step transition from 0 na to 20 nA occurring at t=0, $T_{fsa}$ as indicated above.

To summarize the results shown in FIG. 7, no Rs compensation (case i) results in an error voltage of 100 mV (20 nA*5 Meg) with a time constant=250 µs. Steady-state Rs compensation (case ii) drives the error voltage to 0, but only after ~2 ms, with no increase in bandwidth (time constant= 250 µs). 94% Rs compensation (case iii) reduces the effective series resistance by 94%, resulting in a constant error voltage (6 mV=20 na*Reff) and $\tau_{comp}$=16 µs (10 kHz bandwidth). In all these cases, the resulting error voltage is >2 mV within the crucial time window of 200 µs, which leads to a loss of voltage control when voltage clamping excitable cells.

In contrast the FSA of the present invention (case iv and case v) drives the error voltage to <2 mV in ~200 µs (case iv) or <100 µs (case v) while still maintaining a 10 kHz bandwidth, as required to maintain voltage control of excitable cells. Therefore, only the FSA of the present invention results in series resistance compensation sufficient to voltage clamp excitable cells.

OPERATION OF INVENTION

The present invention consists of placing filter means 36 inside a standard Rs compensation feedback loop. As such, using the present invention is similar to using standard Rs compensation commonly in use, but with the added requirement of first setting the FSA time constants $\tau_{zero}$ and $\tau_{vc}$ (see equation 2). As outlined in the Theory section, $\tau_{vc}$ roughly sets the voltage clamp bandwidth. If $\tau_{vc}$ is set too low (corresponding to very high voltage clamp bandwidth), $T_{fsa} \rightarrow 1$ which is equivalent to prior art standard Rs compensation, with the same inherent limitations outlined earlier. Consequently, $\tau_{vc}$ should only be set as low as necessary to achieve sufficient bandwidth to voltage clamp the expected ionic currents. Usually, setting $\tau_{vc}$ at ~16 µs (corresponding to a bandwidth of ~10 kHz) is sufficient to voltage clamp ionic current in excitable cells.

In practice, a straightforward method of setting $\tau_{vc}$ and $\tau_{zero}$ is to fix the value of $\tau_{vc}$ at a desired voltage clamp bandwidth, and to select the value of $\tau_{zero}$ according to the access time constant $\tau_a$ of the particular electrode/cell combination. Using the preferred embodiment of FIG. 3B, this corresponds to fixing R1 and C, and making R2 a variable potentiometer. It is straightforward to calibrate the range of the potentiometer to correspond to the range of $\tau_a$ observed during an experiment. Determining $\tau_a$ need only be approximate, and can be done by applying voltage clamp pulses and measuring the current transient amplitude and decay time before series resistance compensation is applied.

Alternatively, the value of $\tau_{zero}$ can be preset to the approximate access time constant expected, and $\tau_{vc}$ can be chosen to set the voltage clamp bandwidth. Using the preferred embodiment this corresponds to fixing R2 and C and making R1 a variable potentiometer, allowing the voltage clamp bandwidth to be selected.

CONCLUSIONS, RAMIFICATIONS, AND SCOPE

Accordingly, the reader will see that the frequency-selective attenuator (FSA) of the present invention greatly improves series resistance compensation by eliminating the tradeoff of steady-state error versus bandwidth plaguing the prior art. Prior art standard Rs compensation achieves low steady-state error only at unattainably high bandwidths; prior art steady-state Rs compensation achieves low steady-state error only at unacceptably low bandwidths. In contrast, the present invention eliminates steady-state error while still maintaining sufficient bandwidth to voltage clamp rapid ionic current in excitable cells. Furthermore, the FSA of the present invention

- allows the voltage clamp bandwidth to be independently selected while eliminating steady-state error;
- greatly improves stability by reducing the sensitivity to distributed pipette capacitance; and
- greatly improves stability by reducing, the sensitivity to electrode parameter changes.

A further, related advantage of the FSA is that it allows overcompensation when α is >1. This is useful if the electrode resistance suddenly decreases during an experiment, as happens periodically when the membrane around the electrode shifts unexpectedly due to suction or changing fluid levels. In contrast, standard Rs compensation is unstable when overcompensated under any circumstances.

Although the above description contains many specificities, these should not be construed as limiting the scope of the invention but as merely providing illustrations of some presently preferred embodiments of this invention. Many other embodiments of the FSA are immediately apparent to one skilled in the art. For example, many operational amplifier filter circuits exist to implement the transfer given by equation E2 which would perform equally well as the passive implementation described here as the preferred embodiment. In addition, the transfer function could easily be implemented digitally using a suitably fast digital signal processor equipped with digital-to-analog and analog-to-digital conversion hardware. Furthermore, the present invention does not require that electrode 10 be a conventional glass patch or microelectrode to function well. Any electrode to used implement a voltage clamp which has a series resistance to be compensated will benefit from the FSA of the present invention. Thus the scope of the invention should be determined by the appended claims and their legal equivalents, rather then by the examples given.

I claim:

1. A machine to compensate for series resistance comprising:
   a) a voltage source connected to a cell through an electrode, forming a voltage clamp, said electrode comprising an electrode series resistance and an electrode current, said voltage clamp having an uncompensated time constant proportional to said series resistance and an uncompensated bandwidth inversely proportional to said series resistance, and
   b) a standard series resistance compensation signal proportional to said electrode current, and
   c) a filter means to attenuate said compensation signal, said filter means having a filter input equal to said compensation signal and a filter output, said filter output being added to said voltage source to supply positive feedback to said voltage clamp, said filter means having a lowpass frequency response including:
      i) a corner frequency, said corner frequency being lower in value than said uncompensated bandwidth,
      ii) a roughly unity gain at frequencies below said corner frequency,
      iii) an increasing attenuation, said increasing attenuation beginning at frequencies roughly equal to said corner frequency and ending at frequencies roughly equal to the value of said compensated bandwidth, and
      iv) a roughly constant attenuation at frequencies higher in value than said uncompensated bandwidth,
   wherein said feedback lowers the value of said uncompensated time constant to a compensated time constant and increases the value of said uncompensated bandwidth to a compensated bandwidth, and wherein said filter means enhances the stability of said positive feedback.

2. The machine of claim 1, wherein said filter means has an input-output transfer function comprising:
   a) a zero with a zero time constant roughly equal to said uncompensated time constant,
   b) a pole with a pole time constant greater than said uncompensated time constant, and
   c) a DC gain of roughly unity.

3. The machine of claim 1, wherein said cell includes:
   a) a membrane voltage, and
   b) a membrane current that undergoes a step transition, wherein said membrane voltage in response to said step transition is driven to 0 without compromising said compensated bandwidth.

4. The machine of claim 2, wherein said pole time constant is equal to the sum of said uncompensated time constant and a second time constant, whereby said compensated bandwidth of said voltage clamp is constrained to be roughly equal to the inverse of said second time constant.

5. The machine of claim 4, wherein said filter means is a frequency-selective attenuator comprising:
   a) a first resistor having a resistance R1, a node R1$a$, and a node R1$b$,
   b) a second resistor having a resistance R2, a node R2$a$, and a node R2$b$,
   c) a capacitor having a capacitance C, a node Ca, and a node Cb,
   d) said node R1$a$ serves as said filter input,
   e) said node R1$b$ serves as said filter output,
   f) said node R2$a$ is connected to said node R1$b$,
   g) said node R2$b$ is connected to said node Ca,
   h) said node Cb is grounded, and
   i) the product of R2, times C is roughly equal to said uncompensated time constant, and
   j) the product of R1 times C is roughly equal to said second time constant.

6. A method to compensate for series resistance comprising:
   a) providing a voltage source connected to a cell through an electrode, forming a voltage clamp, said electrode comprising an electrode series resistance and an electrode current, said voltage clamp having an uncompensated time constant proportional to said series resistance and an uncompensated bandwidth inversely proportional to said series resistance, and
   b) providing a standard series resistance compensation signal proportional to said electrode current, and
   c) providing a filter means to attenuate said compensation signal, said filter means having a filter input equal to said compensation signal and a filter output, said filter output being added to said voltage source to supply positive feedback to said voltage clamp, said filter means having a lowpass frequency response including:
      i) a corner frequency, said corner frequency being lower in value than said uncompensated bandwidth,
      ii) a roughly unity gain at frequencies below said corner frequency,
      iii) an increasing attenuation, said increasing attenuation beginning at frequencies roughly equal to said corner frequency and ending at frequencies roughly equal to the value of said compensated bandwidth, and
      iv) a roughly constant attenuation at frequencies higher in value than said uncompensated bandwidth, wherein said feedback lowers the value of said uncompensated time constant to a compensated time constant and increases the value of said uncompensated bandwidth to a compensated bandwidth, and wherein said filter means enhances the stability of said positive feedback.

7. The method of claim 6, wherein said filter means has an input-output transfer function comprising:
   a) a zero with a zero time constant roughly equal to said uncompensated time constant, and
   b) a pole with a pole time constant greater than said uncompensated time constant, and
   c) a DC gain of roughly unity.

8. The method of claim 6, wherein said cell includes:
   a) a membrane voltage, and
   b) a membrane current that undergoes a step transition, wherein said membrane voltage in response to said step transition is driven to 0 without compromising said compensated bandwidth.

9. The method of claim 7, wherein said pole time constant is equal to the sum of said uncompensated time constant and a second time constant, whereby said compensated bandwidth of said voltage clamp is constrained to be roughly equal to the inverse of said second time constant.

10. The method of claim 7, wherein said filter means is a frequency-selective attenuator comprising:
    a) a first resistor having a resistance R1, a node R1$a$, and a node R1$b$,
    b) a second resistor having a resistance R2, a node R2$a$, and a node R2$b$,
    c) a capacitor having a capacitance C , a node Ca, and a node Cb,
    d) said node R1$a$ serves as said filter input,
    e) said node R1$b$ serves as said filter output,
    f) said node R2$a$ is connected to said node R1$b$,
    g) said node R2$b$ is connected to said node Ca,
    h) said node Cb is grounded, and
    i) the product of R2 times C is roughly equal to said uncompensated time constant, and
    j) the product of R1 times C is roughly equal to said second time constant.

11. A method to compensate for series resistance comprising:
    a) providing a voltage source connected to a cell through an electrode, forming a voltage clamp, said electrode comprising an electrode series resistance and an electrode current, said voltage clamp having an uncompensated time constant proportional to said series resistance and an uncompensated bandwidth inversely proportional to said series resistance, and
    b) providing a standard series resistance compensation signal proportional to said electrode current, and
    c) providing a filter means to attenuate said compensation signal, said filter means having a filter input equal to said compensation signal and a filter output, said filter output being added to said voltage source to supply positive feedback to said voltage clamp, said filter means having an input-output transfer function comprising:
       i) a zero with a zero time constant roughly equal to said uncompensated time constant, and
       ii) a pole with a pole time constant greater than said uncompensated time constant, and iii) a DC gain of roughly unity, wherein said feedback lowers the value of said uncompensated time constant to a compensated time constant and increases the value of said uncompensated bandwidth to a compensated bandwidth, and wherein said filter means enhances the stability of said positive feedback.

12. The method of claim 11, wherein said cell includes:

a) a membrane voltage, and b) a membrane current that undergoes a step transition, wherein said membrane voltage in response to said step transition is driven to 0 without compromising said compensated bandwidth.

13. The method of claim 12, wherein said pole time constant is equal to the sum of said uncompensated time constant and a second time constant, whereby said compensated bandwidth of said voltage clamp is constrained to be roughly equal to the inverse of said second time constant.

14. The method of claim 13, wherein said filter means is a frequency-selective attenuator comprising:

a) a first resistor having a resistance R1, a node R1a, and a node R1b, b) a second resistor having a resistance R2, a node R2a, and a node R2b, c) a capacitor having a capacitance C, a node Ca, and a node Cb, d) said node R1a serves as said filter input, e) said node R1b serves as said filter output, f) said node R2a is connected to said node R1b, g) said node R2b is connected to said node Ca, h) said node Cb is grounded, and i) the product of R2 times C is roughly equal to said uncompensated time constant, and j) the product of R1 times C is roughly equal to said second time constant.

15. The method of claim 13, wherein said second resistor is a variable potentiometer.

16. The method of claim 13, wherein said second resistor is a variable potentiometer.

* * * * *